(12) United States Patent
Murali

(10) Patent No.: US 6,193,974 B1
(45) Date of Patent: Feb. 27, 2001

(54) PROCESS OF PREPARING PURIFIED AZADIRACHTIN IN POWDER FORM FROM NEEM SEEDS AND STORAGE STABLE AQUEOUS COMPOSITION CONTAINING AZADIRACHTIN

(75) Inventor: Panchapagesa Muthuswamy Murali, Tamil Nadu (IN)

(73) Assignee: Dalmia Center for Research and Development, Coimbatore (IN)

(*) Notice: Subject to any disclaimer, the term of this patent is extended or adjusted under 35 U.S.C. 154(b) by 0 days.

(21) Appl. No.: 09/141,164

(22) Filed: Aug. 27, 1998

Related U.S. Application Data

(60) Continuation-in-part of application No. 08/937,003, filed on Sep. 24, 1997, now abandoned, which is a division of application No. 08/683,506, filed on Jul. 17, 1996, now Pat. No. 5,736,145.

(30) Foreign Application Priority Data

Jul. 17, 1995 (IN) ........................................ 898/95

(51) Int. Cl.[7] .......................... A61K 35/78; A01N 25/00
(52) U.S. Cl. ..................... 424/195.1; 424/405; 514/453
(58) Field of Search .............................. 424/195.1, 405; 514/453

(56) References Cited

U.S. PATENT DOCUMENTS

| | | | |
|---|---|---|---|
| H1541 | * 6/1996 | Holla | 424/195.1 |
| 4,556,562 | * 12/1985 | Larson | 424/195.1 |
| 4,943,434 | * 7/1990 | Lidert | 424/195.1 |
| 4,946,681 | * 8/1990 | Walter | 424/195.1 |
| 5,001,146 | * 3/1991 | Carter et al. | 514/453 |
| 5,110,591 | * 5/1992 | Williams | 424/195.1 |
| 5,229,007 | * 7/1993 | Ellenberger et al. | 210/690 |
| 5,397,571 | * 3/1995 | Roland et al. | 424/405 |
| 5,420,318 | * 5/1995 | Lidert et al. | 554/193 |

FOREIGN PATENT DOCUMENTS

173327 * 2/1994 (IN) .

* cited by examiner

*Primary Examiner*—Christopher Tate
(74) *Attorney, Agent, or Firm*—Jones Jain, L.L.P.; Chittaranjan N. Nirmel; Mishrilal Jain

(57) ABSTRACT

This invention relates to a process of preparing storage stable aqueous Azadirachtin containing Azadirachtin A to provide a predominant pesticidal composition which comprises the steps of diluting 50,000–100,000 ppm Azadirachtin with 25,000 to 50,000 Azadirachtin A weight/volume with ethanol water solvent in a ratio in the range 100–70:0–30 volume/volume to produce 2,000–40,000 ppm Azadirachtin containing 1,000–20,000 ppm of Azadirachtin A weight/volume. This is followed by emulsifying of the diluted Azadirachtin with non-ionic and non-toxic emulsifying agents in an amount ranging from 0.2 to 30% and neem oil 20–50% volume/volume. The pH of the emulsified diluted Azadirachtin is adjusted to 3.5 to 6.0 by adding an alkali solution. 1–2.5% of a sunscreen like p.aminobenzoic acid or its esters and 1–10% oleic acid volume/volume are added to create a micro-emulsion for stabilizing the composition with a good bio-efficacy.

6 Claims, No Drawings

PROCESS OF PREPARING PURIFIED AZADIRACHTIN IN POWDER FORM FROM NEEM SEEDS AND STORAGE STABLE AQUEOUS COMPOSITION CONTAINING AZADIRACHTIN

This is a Continuation-in-Part of U.S. application Ser. No. 08/937,003 filed Sep. 24, 1997 (now abandoned) which was a Division of U.S. application Ser. No. 08/683,506 filed Jul. 17, 1996 which issued as U.S. Pat. No. 5,736,145 on Apr. 7, 1998.

BACKGROUND OF THE RELATED ART

Several power and effective synthetic insecticides have been used to protect food and fiber crops with varied success for many years now. More recently, there has been a great deal of controversy about the effect of these on the environment and some of the insecticides which have been in extensive use have been banned. It is likely that other insecticides could be banned but which are still in use are considered to be potentially harmful to the environment but are required to be used for lack of other alternatives.

As a result, a search has been going on for "botanical pesticides" which are environmentally friendly. These are compositions which would deter insects or other pests but would have no or minimal harmful effect on the environment, particularly to humans who sometimes are at the end of the food chain and may thus suffer bio-accumulation.

Presently an agent known to protect crops from pests is Azadirachtin which is a natural product found in the seeds of the neem tree (*Azadirachtin indica* A. Juss). This has gained a lot of importance all over the world as the most environmentally safe pesticide. The neem tree is found in great abundance in India and also is distributed in other countries like Pakistan, Bangladesh, Burma, Thailand and Malaysia and is also found in Africa.

Several Azadirachtin isomers, derivatives and related compounds have been studied. From such studies it is evident that Azadirachtin A is the most important compound which has the desired insecticidal property. Azadirachtin A has been extracted from neem seeds and is found to have an anti-feedant property (which deters insects from feeding on plants) and growth regulation potency against such pests. It is readily applied by coating seeds or by applying a spray to the crops themselves.

Various methods of extracting Azadirachtin or such similar principles have been described in Indian patents 153415, 172150, 173327, 173328, 173449, 173989, 173996, 173997 and 173998 and U.S. Pat. Nos. 4,556,562, 5,391,779, 5,372,817, 5,352,677, 5,298,251, 5,281,618, 5,229,007 and 5,124,349. Azadirachtin is a known agent, but stable Azadirachtin A has not been purified to a higher content through a process which enriches the content to about 60–75% of the total Azadirachtin content without the use of laborious columns. The commercial uses of Azadirachtin A have been based on its stability and purification and nowhere in the above patents is a process for purifying and enriching Azadirachtin A described.

U.S. Pat. No. 5,736,145, upon which the present application relies for its teaching of a successful method of extracting Azadirachtin A from neem seeds is incorporated herein by reference.

SUMMARY OF THE INVENTION

It is therefore a principal object of this invention to prepare Azadirachtin A rich extract from total Azadirachtin, with emphasis on a stable and purified form.

To achieve the objective, this invention provides a process of preparing storage stable aqueous Azadirachtin containing Azadirachtin A predominant pesticidal composition, which comprises the steps of:

diluting 50,000–100,000 ppm Azadirachtin with 25,000 to 50,000 Azadirachtin A weight/volume with ethanol water solvent in a ratio 100–70:0–30 volume/volume to 2000–40000 ppm Azadirachtin containing 1000–20000 ppm of Azadirachtin A weight/volume;

emulsifying the diluted Azadirachtin with non-ionic and non-toxic emulsifying agents as herein described in an amount ranging from 0.2 to 30% and neem oil 20–50% volume/volume;

adjusting the pH of emulsified diluted Azadirachtin to 3.5 to 6.0 by adding alkali solution; and adding 1–2.5% of a sunscreen comprising one of p.aminobenzoic acid or its esters and 1–10% oleic acid volume/volume, to create a micro-emulsion for stabilizing the composition with a good bio-efficacy.

Preferred non-ionic and non-toxic emulsifying agents used in the process are sorbitan esters, ethoxylated and propoxylated mono or diglycerides, acetylated mono or diglycerides, lactylated mono, or diglycerides citric acid esters of mono or diglycerides, sugar esters, polysorbates and polyglycerol esters. A preferred emulsifier is polyoxyethylene sorbitan monolaurate which is sold under the name "Tween 20 (R)"

The alkali solution preferably used in the process is $NH_4OH$, and the emulsifying agent preferably used is 15–25% volume/volume of the composition.

An oleic acid, preferably 1% volume/volume of the composition, is added to create a micro-emulsion for stability with a good bio-efficacy.

DETAILED DESCRIPTION OF THE PREFERRED EMBODIMENTS

The step of forming neem kernels pellets involves decortication of the seed either manually or using a decorticator, i.e., a known mechanism for shelling nuts.

The extraction of 80% enriched Azadirachtin A without oozing oil is carried out using acetone and water solvent (hereinafter referred to as the "extracting agent") in the ratio 90; 10 at 80° C. by involving multiple passes of the acetone and water solvent through the neem kernels.

This involves, for example, passing a batch of the extracting agent through the kernels and recovering it and then passing another batch of the extracting agent through the kernels again, and continuing this process until a total of 3 to 5 passes occur. The extract is filtered using an ordinary filter paper to remove clay, sand and some scum. The extract is then washed several times with dichloromethane. The dichloromethane extract is pooled, and moisture removed therefrom with anhydrous sodium sulphate. Dichloromethane is removed, distilled and recovered. Azadirachtin enriched in Azadirachtin A is stuck on the walls of the container and is scraped and collected. Dichloremethane is used in the process as it is an environmentally friendly solvent.

The process requires diluting of 50,000–100,000 ppm Azadirachtin with 25,000 to 50,000 Azadirachtin A weight/volume. The step of diluting to form an emulsion comprises adding dilutent, preferably ethanol:water in the range 100–70:0–30, and an emulsifying agent along with oleic acid volume/volume comprising from about 2,000 to about 40,000 ppm Azadirachtin comprising 1,000–20,000 ppm of Azadirachtin A weight/volume usually from about 20% to about 25% neem oil. Ethanol:water is preferably in the ratio 70:30 volume/volume.

It is highly preferred to include an emulsifying agent in the composition so that the Azadirachtin and neem oil and any other ingredients are kept uniformly distributed in the composition. The percentage of the composition which is the emulsifier normally depends on the emulsifier which is used and the emulsifying agent that is the active ingredient is used in an amount ranging from about 0.2% to about 25% volume/volume.

Preferred emulsifying agents are those normally utilized in foods, and include sorbitan esters, ethoxylated and propoxylated mono or diglycerides, acetylated mono. or diglycerides, lactylated mono. or diglycerides citric acid esters of mono. or diglyerides, sugar esters, polysorbates and polyglycerol esters. The preferred emulsifier is polyoxyethylene sorbitan monolaurate which is solid under the name "Tween 20 (R)".

It is preferred to include oleic acid at a level for example of about 1–10% volume/volume to aid microemulsion preparation and about 1% volume/volume of a sunscreen like P. Amino benzoic acid.

The instant invention will now be described with reference to the following examples:

EXAMPLE I 3 kg of decorticated kernal collected from Tamil Nadu, India, is used in the extraction. Acetone/water in the ratio of 90:10 volume/volume is used for extracting, The extracts are pooled. A minimum of three extractions is required at the elevated temperatures mentioned above, with an optimum of 80° C. as the inner jacket temperature. The first extract is filtered and an equal volume of Dichloromethane is added and extracted. Three extracts of Dicholoromethane of the aqueous extract are pooled. Anhydrous sodium sulphate is added, and water if any in excess is removed. The dichloromethane is distilled and recovered. The enriched Azadirachtin A thus obtained is used further for formulation. To the extract is added Tween 20 (R) (consisting of water and polyoxyethylene sorbitan monolaurate) to obtain a diluted extract containing 3,000 ppm Azadirachtin and 20% neem oil weight/volume. To the resulting emulsion is added ammonium hydroxide to adjust the pH to 4.0. To this is added 1% p-amino benzoic acid or its esters and 1% oleic acid volume/volume for microemulsion purposes. This formulation is an agent against a wide spectrum of pests and is shelf stable for more than 8 weeks after formulation. A product containing 2,000 ppm Azadirachtin A weight/volume minimum and having a pH of 4.0 maintained under normal shelf life conditions (without refrigeration or addition of sunscreen) was found to have retained 65% of its potency even two years later.

EXAMPLE II

Processing is carried out as in Example 1, except that extraction and separation of extract from neem kernels is carried out by centrifuging. The resulting product is effective against a wide spectrum of pests.

What is claimed is:

1. A process for preparing a storage stable Azadirachtin enriched Azadirachtin A pesticidal composition, comprising the steps of:
   (a) passing at least three batches of an aqueous polar solvent through decorticated and pelleted neem seeds to obtain a solvent extract without oozing neem oil from said seeds;
   (b) removing Azadirachtin A from said solvent extract with a polar solvent to obtain an Azadirachtin A solution;
   (c) removing the polar solvent from the Azadirachtin A solution to obtain a concentrated Azadirachtin A solution;
   (d) removing trace oil and hydrophobic impurities from the concentrated Azadirachtin A solution with a non-polar solvent;
   (e) removing water from the concentrated Azadirachtin A solution;
   (f) recovering a substantially purified Azadirachtin A powder;
   (g) diluting the substantially purified Azadirachtin A powder with ethanol:water in proportions in the range 100–70:0–30 (volume/volume) to a concentration of 2000–40,000 ppm Azadirachtin containing 1,000–20,000 ppm of Azadirachtin A (weight/volume);
   (h) emulsifying the diluted Azadirachtin with 0.2% to 30% (volume/volume) of a non-ionic and non-toxic emulsifying agent and adding neem oil in the ratio of 20–50% (volume/volume) of the composition;
   (i) adjusting the pH of the emulsified diluted Azadirachtin to 3.5 to 6.0 by adding an alkali solution; and
   (j) adding 1–2.5% sunscreen agent comprising one of para-amino benzoic acid (PABA) or its ester after pH adjustment to stabilize the resultant composition.

2. A process according to claim 1, wherein:
   the non-ionic and non-toxic emulsifying agent is selected from the group consisting of sorbitan esters, ethoxylated and propoxylated monoglycerides or diglycerides, acetylated monoglycerides or diglycerides, lactylated monoglycerides or diglycerides citric acid esters of monoglycerides or diglycerides, sugar esters, polysorbates and polyglycerol esters, and polyoxyethylene sorbitan monolaurate.

3. A process according to claim 1, wherein the neem oil is added in a ratio 40–45% (volume/volume) of the composition.

4. A process according to claim 1, wherein the alkali solution comprises ammonium hydroxide.

5. A process according to claim further adding 1–10% (volume/volume) of oleic acid to create a microemulsion.

6. A process according to claim 5, wherein 1% (volume/volume) of oleic acid is added.

* * * * *